(12) United States Patent
Struck et al.

(10) Patent No.: US 9,128,107 B2
(45) Date of Patent: Sep. 8, 2015

(54) PROGNOSTIC BIOMARKERS FOR THE PROGRESSION OF PRIMARY CHRONIC KIDNEY DISEASE

(75) Inventors: Joachim Struck, Berlin (DE); Benjamin Dieplinger, Linz (AU); Thomas Muller, Linz (AU); Barbara Kollerits, Innsbruck (AU); Florian Kronenberg, Innsbruck (AU)

(73) Assignee: B.R.A.H.M.S. GMBH, Hennigsdorf (DE)

( * ) Notice: Subject to any disclaimer, the term of this patent is extended or adjusted under 35 U.S.C. 154(b) by 1148 days.

(21) Appl. No.: 13/125,631

(22) PCT Filed: Oct. 22, 2009

(86) PCT No.: PCT/EP2009/007739
§ 371 (c)(1),
(2), (4) Date: Sep. 19, 2011

(87) PCT Pub. No.: WO2010/046137
PCT Pub. Date: Apr. 29, 2010

(65) Prior Publication Data
US 2012/0003752 A1    Jan. 5, 2012

(30) Foreign Application Priority Data

Oct. 22, 2008 (EP) .................................. 08167312

(51) Int. Cl.
G01N 31/00   (2006.01)
G01N 33/53   (2006.01)
G01N 33/74   (2006.01)

(52) U.S. Cl.
CPC ............ *G01N 33/74* (2013.01); *G01N 2333/58* (2013.01); *G01N 2800/347* (2013.01)

(58) Field of Classification Search
CPC ... C07K 14/47; G01N 33/74; G01N 2333/95; G01N 2800/50; G01N 2800/52
See application file for complete search history.

(56) References Cited

U.S. PATENT DOCUMENTS

2004/0121343 A1   6/2004  Buechler et al.
2010/0035275 A1   2/2010  Bergmann et al.

FOREIGN PATENT DOCUMENTS

EP   0 721 105        7/1996
GB   2 403 533        1/2005
WO   WO-2008 055491   5/2008

OTHER PUBLICATIONS

Metry et al. (Acta Physiol Scand 2001, 171, 117-122).*
Obineche et al. (Kidney International, 2006, 69, 152-156).*
Bunton, D. C. et al., "The clinical relevance of adrenomedullin: a promising profile?" Pharmacology & Therapeutics, 2004, vol. 103, pp. 179-201.
Franz, M. et al., "N-terminal fragments of the proatrial natriuretic peptide in patients before and after hemodialysis treatment," Kidney International, 2000, vol. 58, pp. 374-383.
International Search Report for PCT/EP2009/007739 dated Mar. 17, 2010.
Ishimitsu, T. et al., "Plasma levels of adrenomedullin, a newly identified hypotensive peptide, in patients with hypertension and renal failure," The Journal of Clinical Investigation, Nov. 1994, vol. 94, No. 5, pp. 2158-2161.
Kimura, T. et al., "Left ventricular hypertrophy in predialysis chronic kidney disease: Impact of cardiovascular stress makers," Japanese Journal of Nephrology, Jan. 1, 2007, vol. 49, No. 8, pp. 1007-1013.
Kitamura, K. et al., "Cloning and characterization of cDNA encoding a precursor for human adrenomedullin," Biochemical and biophysical Research Communications, Jul. 30, 1993, vol. 194, No. 2, pp. 720-725.
Mazul-Sunko, B. et al., "Proatrial Natriuretic Peptide (1-98), but not cystatin C, Is predictive for occurrence of acute renal insufficiency in critically III Septic Patients," Nephron Clin Prat, 2004, vol. 97, pp. 103-107.
Metry, G. et al., "Fluid balance in patients with chronic renal failure assessed with N-terminal proatrial natriuretic peptide, atrial natriuretic peptide and ultrasonography," Acta Physiol. Scand., 2001, vol. 171, pp. 117-122.
Miyata, A. et al., "Molecular forms of atrial natriuretic polypeptides circulating in human plasma," Biochemical and biophysical research communications, Jan. 30, 1987, vol. 142, No. 2, pp. 461-467.
Obineche, E. N. et al., "Natriuretic peptide and adrenomedullin levels in chronic renal failure and effects of peritoneal dialysis," Kidney International, 2006, vol. 69, pp. 152-156.
Predel, H. G. et al., "Elevated plasma concentrations and molecular weight heterogeneity of human atrial natriuretic peptide in patients with progressive chronic renal failure," 198S, only English abstract.
Rascher, W. et al., "Atrial natriuretic peptide in plasma of volume-overloaded children with chronic renal failure," Lancet, Aug. 10, 1985, vol. 2, No. 8450, pp. 303-305.
Rutten, J. H. W. et al., "B-type natriuretic peptide and amino-terminal atrial natriuretic peptide predict survival in peritoneal dialysis," Peritoneal Dialysis International, Sep. 1, 2006, vol. 26, No. 5, pp. 598-602.
Shin-Ich, I. et al., "Prognostic significance of elevated plasma brain natriuretic poly peptide in patients with chronic renal failure treated with hemodialysis," JACC, Mar. 6, 2002, 1206-172.
Tikkanen, I. et al., "Plasma level of atrial natriuretic peptide as an indicator of increased cardiac load in uremic patients," Clinical Naphrology, 1990, vol. 34, No. 4, pp. 167-172.
Vesely, D. et al., "Atrial natriuretic peptides in pathophysiological disease," Cardiovascular Research, 2001, vol. 51, pp. 647-658.
Von Haehling, S. et al., "Comparison of Midregional pro-atrial natriuretic peptide with n-terminal pro-b-type natriuretic peptide in predicting survival in patients with chronic heart failure," Journal of the American College of Cardiology, Oct. 29, 2007, vol. 50, No. 20, pp. 1973-1980.

* cited by examiner

*Primary Examiner* — Lisa Cook
(74) *Attorney, Agent, or Firm* — Millen, White, Zelano, Branigan, P.C.

(57) ABSTRACT

Subject of the present invention are assays and in vitro methods for prediction of the progression of primary chronic kidney disease (CKD) or for monitoring chronic kidney disease therapy comprising the determination of the level of ANP and/or ADM or its precursors or fragments thereof.

15 Claims, 6 Drawing Sheets

Fig. 1

SEQ ID NO:1 (amino acid sequence of pre-pro-ADM):

```
1    MKLVSVALMY LGSLAFLGAD TARLDVASEF RKKWNKWALS RGKRELRMSS
51   SYPTGLADVK AGPAQTLIRP QDMKGASRSP EDSSPDAARI RVKRYRQSMN
101  NFQGLRSFGC RFGTCTVQKL AHQIYQFTDK DKDNVAPRSK ISPQGYGRRR
151  RRSLPEAGPG RTLVSSKPQA HGAPAPPSGS APHFL
```

Fig. 2

SEQ ID NO:2 (amino acid sequence of pro-ADM):

```
1    ARLDVASEFR KKWNKWALSR GKRELRMSSS YPTGLADVKA GPAQTLIRPQ
51   DMKGASRSPE DSSPDAARIR VKRYRQSMNN FQGLRSFGCR FGTCTVQKLA
101  HQIYQFTDKD KDNVAPRSKI SPQGYGRRRR RSLPEAGPGR TLVSSKPQAH
151  GAPAPPSGSA PHFL
```

Fig. 3

SEQ ID NO:3 (amino acid sequence of pro-ADM N20):

```
1    ARLDVASEFR KKWNKWALSR
```

Fig. 4

SEQ ID NO:4 (amino acid sequence of MR-pro-ADM):

```
1    ELRMSSSYPT GLADVKAGPA QTLIRPQDMK GASRSPEDSS
```

Fig. 5

SEQ ID NO:5 (amino acid sequence of ADM):

```
1    YRQSMNNFQG LRSFGCRFGT CTVQKLAHQI YQFTDKDKDN VAPRSKISPQ
51   GY
```

Fig. 6

SEQ ID NO:6 (amino acid sequence of pre-pro-ANP):

```
1    MSSFSTTTVS FLLLLAFQLL GQTRANPMYN AVSNADLMDF KNLLDHLEEK
51   MPLEDEVVPP QVLSEPNEEA GAALSPLPEV PPWTGEVSPA QRDGGALGRG
101  PWDSSDRSAL LKSKLRALLT APRSLRRSSC FGGRMDRIGA QSGLGCNSFR
151  YRR
```

Fig. 7

SEQ ID NO:7 (amino acid sequence of pro-ANP):

```
1    NPMYNAVSNA DLMDFKNLLD HLEEKMPLED EVVPPQVLSE PNEEAGAALS
51   PLPEVPPWTG EVSPAQRDGG ALGRGPWDSS DRSALLKSKL RALLTAPRSL
101  RRSSCFGGRM DRIGAQSGLG CNSFRY
```

Fig. 8

SEQ ID NO:8 (amino acid sequence of ANP):

```
1    SLRRSSCFGG RMDRIGAQSG LGCNSFRY
```

Fig. 9

SEQ ID NO:9 (amino acid sequence of NT-proANP):

```
1    NPMYNAVSNA DLMDFKNLLD HLEEKMPLED EVVPPQVLSE PNEEAGAALS
51   PLPEVPPWTG EVSPAQRDGG ALGRGPWDSS DRSALLKSKL RALLTAPR
```

Fig. 10

SEQ ID NO:10 (amino acid sequence of amino acids 53-90 of proANP):

```
1    PEVPPWTGEV SPAQRDGGAL GRGPWDSSDR SALLKSKL
```

PROGNOSTIC BIOMARKERS FOR THE PROGRESSION OF PRIMARY CHRONIC KIDNEY DISEASE

This application is a National Stage entry of PCT/EP2009/007739 filed on Oct. 22, 2009, which claims priority to EP 08 167 312.1 filed on Oct. 22, 2008.

SEQUENCE LISTING

The instant application contains a Sequence Listing which has been submitted in ASCII format via EFS-Web and is hereby incorporated by reference in its entirety. Said ASCII copy, created on Apr. 11, 2011, is named SQL.txt and is 8,692 bytes in size.

FIELD OF THE INVENTION

The present invention is in the field of prognostic biomarkers and relates to the prediction of the outcome for patients with chronic kidney disease.

BACKGROUND OF THE INVENTION

Chronic kidney disease (CKD) is a major health problem with increasing incidence and prevalence, high costs, and poor outcomes. Introduction of the Kidney Disease Outcome Quality Initiative (K/DOQI) classification and the use of estimated glomerular filtration rate (eGFR) to assess renal function have identified large numbers of patients with previously undiagnosed CKD (National Kidney Foundation. Am J Kidney Dis 2002; 39 (2 Suppl 1): S1-266; Centers for Disease Control and Prevention (CDC), Morb Mortal Wkly Rep 2007; 56: 161-165). However, only a minority of CKD patients ever advance to end-stage renal disease (ESRD) (Clase et al., BMJ 2004; 329: 912-915). The identification of those patients with the greatest risk for CKD progression remained a challenge. Through the adoption of the K/DOQI recommendations and routinely reported estimates of GFR by many laboratories, substantial success has been achieved in screening for undiagnosed CKD. However, there is an urgent need for further risk stratification and the identification of further risk predictors to target interventions to those patients with CKD most likely to progress to ESRD.

Amino-terminal proBNP (NT-proBNP), a well established prognostic marker for cardiovascular disease, has been shown to predict kidney disease progression in non-diabetic patients with primary CKD (Spanaus et al., Clin Chem 2007; 53: 1264-1272).

A-type natriuretic peptide (ANP) and adrenomedullin (ADM) are potent hypotensive, diuretic, and natriuretic peptides involved in maintaining cardiovascular and renal hemostasis (Vesely et al., Cardiovasc Res 2001; 51: 647-658; Bunton et al., Pharmacol Ther 2004; 103: 179-201). Increased plasma concentrations of ANP and ADM have been reported in patients with cardiovascular disease and in patients with kidney disease (Lerman et al., Lancet 1993; 341: 1105-1109; Jougasaki et al., Circulation 1995; 92:286-289; Winters et al., Biochem Biophys Res Commun 1988; 150: 231-236; Ishimitsu et al., J Clin Invest 1994; 94: 2158-2161). However, ANP and ADM have never been considered as markers to predict the progression of kidney disease.

The peptide Adrenomedullin (ADM) was first described in 1993 (Kitamura et al. (1993), Biochem. Biophys. Res. Commun. 192:553-560) as a novel hypotensive peptide comprising 52 amino acids, which had been isolated from a human pheochromocytoma. In the same year, cDNA coding for a precursor peptide comprising 185 amino acids and the complete amino acid sequence of this precursor peptide were also described (Kitamura et al. (1993), Biochem. Biophys. Res. Commun. 194:720-725). The precursor peptide, which comprises, inter alia, a signal sequence of 21 amino acids at the N-terminus, is referred to as "pre-pro-Adrenomedullin" (pre-pro-ADM).

The ADM peptide comprises amino acids 95 to 146 of pre-pro-ADM, from which it is formed by proteolytic cleavage. Some peptide fragments of those formed in the cleavage of the pre-proADM have been characterized in detail, in particular the physiologically active peptides adrenomedullin (ADM) and "PAMP", a peptide comprising 20 amino acids (22-41) which follow the 21 amino acids of the signal peptide in pre-proADM. Another fragment of unknown function and high ex vivo stability is midregional proAdrenomedullin (MR-proADM) (Struck et al. (2004), Peptides 25(8):1369-72), for which a reliable quantification method has been developed (Morgenthaler et al. (2005), Clin. Chem. 51(10): 1823-9).

The discovery and characterization of ADM in 1993 triggered intensive research activity and a flood of publications, the results of which have recently been summarized in various review articles, in the context of the present description, reference is being made in particular to the articles to be found in an issue of "Peptides" devoted to ADM (Peptides 22 (2001)), in particular (Takahashi (2001), Peptides 22, 1691 and Eto (2001), Peptides 22, 1693-1711). The subject is further reviewed in Hinson et al. (Hinson et al. (2000), Endocr. Rev. 21 (2), 138-167). ADM may be regarded as a polyfunctional regulatory peptide. It is released into the circulation in an inactive form extended by a C-terminal glycine (Kitamura et al. (1998), Biochem. Biophys. Res. Commun. 244 (2), 551-555).

ADM is an effective vasodilator. The hypotensive effect has been associated particularly with peptide segments in the C-terminal part of ADM. Peptide sequences of the N-terminus of ADM on the other hand exhibit hypertensive effects (Kitamura et al. (2001), Peptides 22, 1713-1718).

Atrial natriuretic peptide (ANP, also known as atrial natriuretic factor (ANF)) is a peptide hormone comprising 28 amino acid residues (SEQ ID NO:8). The ANP gene comprises 3 exons and 2 introns and codes for a 153 amino acid pre-proANP (SEQ ID NO:6). Upon cleavage of an N-terminal signal peptide (25 amino acids) and the two C-terminal amino acids (127/128), proANP is released. ANP comprises residues 99-126 from the C-terminus of the precursor prohormone proANP (SEQ ID NO:7). This prohormone is cleaved into the mature 28 amino acid peptide ANP, also known as ANP (1-28) or α-ANP, and the amino terminal fragment ANP (1-98) (NT-proANP, SEQ ID NO:9). Thus, NT-proANP and ANP are produced in equimolar amounts. The 98 amino acid NT-proANP may be further processed proteolytically. Midregional proANP (MR-proANP) is defined as proANP or any fragments thereof comprising at least amino acid residues 53-90 of proANP. Amino acids 53 to 90 of proANP are illustrated in SEQ ID NO:10 (FIG. 10). Measurement of MR-proANP has been used in differential diagnosis of acute decompensated heart failure (Gegenhuber et al., Clin Chem 2006; 52: 827-31).

Concerning ANP and precursors and fragments thereof, several publications deal with measurements of these analytes in patients with advanced kidney disease, in particular before and after hemodialysis. In these publications the measured levels of analytes are analyzed with respect to their association to other parameters, which have been obtained from the patients at the same time as the samples were obtained for measurement. None of the publications has followed the development of the disease over time, and thus cannot and does not make investigations on whether an analyte level measured at a given time point is associated with an increase in the severity of the disease, i.e. whether an analyte level can be suitable for the prediction of the progression of the disease. Nephron. 1991; 58(1):17-22. Change in plasma immunoreactive N-terminus, C-terminus, and 4,000-dalton midportion of atrial natriuretic factor prohormone with hemodialysis. Winters C J, Vesely D L. Regul Pept Suppl.1985; 4:110-2. Plasma concentration of atrial natriuretic polypeptide in chronic hemodialysis patients. Yamamoto Y, Higa T, Kitamura K, Tanaka K, Kangawa K, Matsuo H.

DETAILED DESCRIPTION OF THE INVENTION

The present invention relates to a method for prediction of the progression of primary chronic kidney disease (CKD) or for monitoring chronic kidney disease therapy, comprising the following steps:
 (a) providing a sample from a patient suffering from primary chronic kidney disease,
 (b) determining the level of ANP and/or ADM or fragments thereof or its precursors or fragments thereof,
 (c) correlating the level of ANP and/or ADM or fragments thereof or its precursors or fragments thereof with the prediction of the progression of primary chronic kidney disease.

In one preferred embodiment the present invention relates to a method for prediction of the progression of primary chronic kidney disease (CKD), comprising the following steps:
 (a) providing a sample from a patient suffering from primary chronic kidney disease,
 (b) determining the level of ANP and/or ADM or fragments thereof or its precursors or fragments thereof,
 (c) correlating the level of ANP and/or ADM or fragments thereof or its precursors or fragments thereof with the prediction of the progression of primary chronic kidney disease.

In another preferred embodiment the present invention relates to a method for monitoring chronic kidney disease therapy, comprising the following steps:
 (a) providing a sample from a patient suffering from primary chronic kidney disease,
 (b) determining the level of ANP and/or ADM or fragments thereof or its precursors or fragments thereof,
 (c) correlating the level of ANP and/or ADM or fragments thereof or its precursors or fragments thereof with the prediction of the progression of primary chronic kidney disease.

The most preferred embodiment is the method for prediction of the progression of primary kidney disease as described above. This is the most valuable embodiment. This method for prediction can be varied with all the specific embodiments outlined herein later. The method allows for the discrimination of patients with progressing chronic kidney disease from patients with non-progressing chronic kidney disease. Progressing CKD herein relates to CKD that advances and possibly advances to doubling serum creatinine and end-stage renal disease (ESRD). Thus, in a preferred embodiment of the method the patient is being classified as a progressor or a non-progressor. A progressor is thus a patient whose CKD will eventually advance into end-stage renal disease (ESRD). This means in one embodiment a progressor is defined as a patient that progresses to the endpoint which was doubling serum creatinine preferably without reaching ESRD. ESRD is an uncompensable renal disease. This means that the renal damage is not reversible anymore and dialysis or transplantation is needed.

This means the preferred patient subgroup for the method for prediction of the progression of primary CKD and/or for monitoring kidney disease encompasses exclusively patients that are not in the ESRD.

In another embodiment of the invention a progressor is defined as a patient that progresses to the endpoint ESRD requiring renal replacement. Progression is thus defined as a process of the disease from mild to moderate kidney disease towards one of the before mentioned endpoints which are either doubling serum creatinine preferably without reaching ESRD or reaching ESRD requiring renal replacement. The methods of the present invention are especially applicable to patients with mild to moderate kidney disease. Patients with mild to moderate disease are defined as patients having a stable renal function for at least 3 months before measurement of analytes. In a preferred embodiment patients with mild to moderate disease do not require hemodialysis.

In a preferred embodiment the methods of the present invention are for predicting progression or monitoring the chronic kidney disease but not predicting the risk of mortality. Thus, according to one embodiment of the present invention mortality is not an endpoint which was considered for the classification of patients into progressors or non-progressors. It is however clear to a person skilled in the art that a progressor may have an enhanced risk of mortality in comparison to a non-progressor.

In one preferred embodiment the present invention relates to a method for prediction of the progression of primary chronic kidney disease (CKD) or for monitoring chronic kidney disease therapy for patients with mild to moderate kidney disease, comprising the following steps:
 (a) providing a sample from a patient suffering from primary chronic kidney disease with mild to moderate kidney disease,
 (b) determining the level of ANP and/or ADM or fragments thereof or its precursors or fragments thereof,
 (c) correlating the level of ANP and/or ADM or fragments thereof or its precursors or fragments thereof with the prediction of the progression of primary chronic kidney disease.

In one preferred embodiment the present invention relates to a method for prediction of the progression of primary chronic kidney disease (CKD) or for monitoring chronic kidney disease therapy for patients with mild to moderate kidney disease, comprising the following steps:
 (a) providing a sample from a patient suffering from primary chronic kidney disease with mild to moderate kidney disease,
 (b) determining the level of ANP and/or ADM or fragments thereof or its precursors or fragments thereof,
 (c) correlating the level of ANP and/or ADM or fragments thereof or its precursors or fragments thereof with the prediction of the progression of primary chronic kidney disease without taking the prediction of mortality into account.

This means progression of primary chronic kidney disease, where progression means worsening of kidney function. A measure of worsening of kidney function is an increase, i.e. at least a doubling of baseline serum creatinine and/or ESRD necessitating renal replacement therapy In one preferred embodiment of the invention the level of ANP or fragments thereof or its precursors or fragments thereof is determined and used as single marker. In another preferred embodiment of the invention the level of ADM or fragments thereof or its precursors or fragments thereof is determined and used as single marker.

ANP or fragments thereof or its precursors or fragments thereof are preferably selected from the group comprising NT-proANP, MR-proANP and mature ANP or fragments thereof. Fragments may have preferably at least 12 amino acids in length.

ADM or fragments thereof or its precursors or fragments thereof are preferably selected from the group comprising mature ADM, MR-proADM, PAMP and CT-proADM or fragments thereof. Fragments may have preferably at least 12 amino acids in length.

In particularly preferred embodiments of the invention the prediction of the progression of primary chronic kidney disease may be improved by additionally determining and using the level of at least one further laboratory parameter or a further marker selected from the group comprising: creatinine, GFR ("glomerular filtration rate"; GFR may for example be determined by measuring iohexol-clearance (Bostom et al., J Am Soc Nephrol 2002; 13: 2140-2144)), Proteinuria, albumin, C-reactive protein (CRP), Cystatin C, growth differentiation factor 15 (GDF15), interleukin 1 receptor-like 1 (ST2), Neutrophil Gelatinase-Associated Lipocalin (NGAL), Procalcitonin and fragments thereof, BNP or fragments thereof or its precursors or fragments thereof, particularly proBNP or NT-proBNP, pro-Vasopressin and fragments thereof including copeptin, vasopressin and neurophysin II, pro-Endothelin-1 and fragments thereof including CT-proET-1, NT-proET-1, big-Endothelin-1 and Endothelin-1.

It is also preferred that additionally at least one clinical parameter is determined selected from the group comprising: age, gender, systolic blood pressure, diastolic blood pressure, body mass index, current smoking habits, antihypertensive treatment.

The present invention also pertains to a method for prediction of the progression of primary chronic kidney disease and for monitoring chronic kidney disease therapy as described above, wherein the level of ANP and/or ADM or precursors or fragments thereof either alone or in conjunction with other prognostically useful laboratory or clinical parameters is used for the prediction of the progression of primary chronic kidney disease by a method which may be selected from the following alternatives:
  Comparison with the median of the level of ANP and/or ADM or its precursors or fragments thereof in an ensemble of pre-determined samples in a population of patients having primary chronic kidney disease,
  Comparison with a quantile of the level of ANP and/or ADM or its precursors or fragments thereof in an ensemble of pre-determined samples in a population of patients having primary chronic kidney disease,
  Calculation based on Cox Proportional Hazards analysis or by using Risk index calculations such as the NRI (Net Reclassification Index) or the IDI (Integrated Discrimination Index).

In a particular embodiment the level of MR-proADM is measured using a diagnostic assay comprising one or more capture probes directed against one ore more epitopes located in amino acid positions 45-92 of pre-proADM.

In a further aspect the present invention also relates to the use of ANP and/or ADM or fragments thereof or its precursors or fragments thereof for the prediction of renal endpoints in a patient suffering from primary chronic kidney disease.

Furthermore, the invention pertains to the use of ANP and/or ADM or fragments thereof or its precursors or fragments thereof for the prediction of the progression of primary chronic kidney disease.

In one embodiment of the invention, the patient suffering from primary chronic kidney disease does not suffer from diabetes mellitus. Thus, in a preferred embodiment of the invention, chronic kidney disease is a non-diabetic chronic kidney disease.

Also within the scope of the present invention is the use of ANP and/or ADM or fragments thereof or its precursors or fragments thereof for the classification of a patient suffering from primary chronic kidney disease into progressor or a non-progressor.

Particularly, ANP and/or ADM or fragments thereof or its precursors or fragments thereof are used as GFR independent predictor and classification marker.

The present invention also relates to the use of any of the methods of the invention for monitoring the success of a therapy for chronic kidney disease in a patient suffering from primary chronic kidney disease. In this context the methods of the present invention may be applied at one or more times after the start of a therapy and the results may be compared to each other or to the result before the start of the therapy in order to assess the success of the therapy.

Also within the scope of the present invention is the use of any method according to the invention for monitoring kidney function.

In one embodiment an MR-proADM assay having a detection limit below 0.3 nmol/L and/or below the median of a population of patients having primary chronic kidney disease and an interassay precision of <30% CV in the normal range is used for the prediction of the progression of primary chronic kidney disease.

In another embodiment an MR-proANP assay having a detection limit below 20 pmol/L and/or below the median of a population of patients having primary chronic kidney disease and an interassay precision of <30% CV in the normal range is used for the prediction of the progression of primary chronic kidney disease.

The present invention also relates to the use of a capture probe directed against ANP or fragments thereof or its precursors or fragments thereof and/or ADM or fragments thereof or its precursors or fragments thereof for predicting the progression of primary chronic kidney disease. In case of ADM, preferably, said capture probes are directed against one ore more epitopes located in amino acid positions 45-92 of pre-proADM. In case of ANP, preferably, said capture probes are directed against one ore more epitopes located in amino acid positions 53-90 of proANP.

In general, fragments of the peptides and precursor peptides as defined herein relate to fragments thereof of at least 12 amino acids in length. Fragments are preferably immunologically detectable fragments of the peptides.

In the context of the present invention, the term "pro-Adrenomedullin" (proADM) and the term "pro-Adrenomedullin or fragments thereof" refer to either the entire molecule of proADM or fragments thereof of at least 12 amino acids including but not limited to ADM, PAMP and MR-proADM. In a preferred embodiment, proADM refers to either the entire molecule of proADM or fragments thereof of at least 12 amino acids with the exception of mature ADM. In a further preferred embodiment, proADM refers to either the entire molecule of proADM or fragments thereof of at least 12 amino acids with the exception of mature ADM or fragments of mature ADM. Thus, in one particular embodiment of the invention "determining the level of proADM or fragments thereof" refers to determining the level of proADM or fragments thereof, wherein the level of mature ADM and/or fragments of mature ADM is not determined.

The amino acid sequence of the precursor peptide of Adrenomedullin (pre-pro-Adrenomedullin) is given in FIG. 1 (SEQ ID NO:1). Pro-Adrenomedullin relates to amino acid residues 22 to 185 of the sequence of pre-pro-Adrenomedullin. The amino acid sequence of pro-Adrenomedullin (pro-ADM) is given in FIG. 2 (SEQ ID NO:2). The pro-ADM N-terminal 20 peptide (PAMP) relates to amino acid residues 22-41 of pre-proADM. The amino acid sequence of PAMP is given in FIG. 3 (SEQ ID NO:3). MR-pro-Adrenomedullin (MR-pro-ADM) relates to amino acid residues 45-92 of pre-pro-ADM. The amino acid sequence of MR-pro-ADM is provided in FIG. 4 (SEQ ID NO:4). The amino acid sequence of mature Adrenomedullin (ADM) is given in FIG. 5 (SEQ ID NO:5).

The amino acid sequence of ANP is given in FIG. 8 (SEQ ID NO:8). The sequence of the 153 amino acid pre-proANP is shown in FIG. 6 (SEQ ID NO:6). Upon cleavage of an N-terminal signal peptide (25 amino acids) and the two C-terminal amino acids (127/128) proANP (FIG. 7, SEQ ID NO:7) is released. ANP comprises residues 99-126 from the C-terminus of the precursor prohormone pro-ANP. This prohormone is cleaved into the mature 28 amino acid peptide ANP, also known as ANP (1-28) or α-ANP, and the amino terminal fragment ANP (1-98) (NT-proANP, FIG. 9, SEQ ID NO:9). Mid-regional proANP (MR-proANP) is defined as NT-proANP or any fragments thereof comprising at least amino acid residues 53-90 (SEQ ID NO:10 in FIG. 10) of proANP.

As mentioned herein in the context of proteins or peptides, the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds.

In the context of the present invention, the term "level" in expressions such as "level of a protease", "analyte level" and similar expressions, refers to the quantity of the molecular entity mentioned in the respective context, or in the case of enzymes it can also refer to the enzyme activity.

In one preferred embodiment of the method of the invention said level of Pro-Adrenomedullin or fragments thereof and/or proANP or fragments thereof is determined and used as single marker.

In particularly preferred embodiments of the invention the prediction of the progression of primary chronic kidney disease may be improved by additionally determining and using the level of at least one further laboratory parameter selected from the group comprising: creatinine, GFR ("glomerular filtration rate"; GFR may for example be determined by measuring iohexol-clearance (Bostom et al., J Am Soc Nephrol 2002; 13: 2140-2144)), Proteinuria, albumin, CRP, Cystatin C, GDF15, ST2, NGAL, Procalcitonin and fragments thereof, BNP or fragments thereof or its precursors or fragments thereof, particularly proBNP or NT-proBNP, pro-Vasopressin and fragments thereof including copeptin, vasopressin and neurophysin II, pro-Endothelin-1 and fragments thereof including CT-proET-1, NT-proET-1, big-Endothelin-1 and Endothelin-1.

The term "additionally determining" does not imply, albeit not exclude, that such determinations are technically combined. The term "additionally using" is defined as any kind of mathematical combination of parameters—be it laboratory and/or clinical parameters—that yield a prediction of the progression of primary chronic kidney disease. One example of such mathematical combination is the Cox proportional hazards analysis, from which the risk of a subject suffering from primary chronic kidney disease for progression of the disease can be derived, but other methods maybe used as well.

The invention also involves comparing the level of marker for the individual with a predetermined value. The predetermined value can take a variety of forms. It can be single cut-off value: This can be for instance a median or mean or the $75^{th}$, $90^{th}$, $95^{th}$ or $99^{th}$ percentile of a reference population. This can be for instance also an "optimal" cut-off value. The optimal cut-off value for a given marker is the value where the product of diagnostic sensitivity and specificity is maximal for this marker. Diagnostic sensitivity is the relative fraction of patients, carrying the disease or the risk for developing the disease (depending on the diagnostic or prognostic question to be answered in any particular case), which are correctly recognized as such by a marker ("true positives"), and the diagnostic specificity is the relative fraction of patients, not carrying the disease or the risk for developing the disease (depending on the diagnostic or prognostic question to be answered in any particular case), which are recognized as such by a marker ("true negatives"). This can by a cut-off value optimized for a maximal negative predictive value or maximal positive predictive value, depending on clinical or economical needs.

Thus, one might adopt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

The predetermined value can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk.

The predetermined value can vary among particular reference populations selected, depending on their habits, ethnicity, genetics etc. Accordingly, the predetermined values selected may take into account the category in which an individual falls. Appropriate ranges and categories can be selected with no more than routine experimentation by those of ordinary skill in the art.

The usefulness of various threshold levels, as discussed above, can be visualized for instance by Kaplan-Meier plots (FIG. 11-14), where the occurrence of events i.e. in the present case: kidney disease progression, over time is depicted for subgroups of the investigated patient population: Here, for four Kaplan-Meier analyses, the investigated patient population has been separated in two subgroups each. The subgroups were defined as follows:

a) the investigated patient population separated in one group having MR-proANP values above the median level (106 pmol/L) and another group having MR-proANP values below the median level (FIG. 11),
b) the investigated patient population separated in one group having MR-proADM values above the median level (0.75 nmol/L) and another group having MR-proADM values below the median level (FIG. 12),
c) the investigated patient population separated in one group having MR-proADM values above the optimum threshold-level (0.865 nmol/L (sensitivity of 0.766 and a specificity of 0.809)) and another group having MR-proADM values below the optimum threshold-level (FIG. 13), d) the investigated patient population separated in one group having MR-proANP values above the optimum threshold-level (84.15 pmol/L (sensitivity of 0.891 and a specificity of 0.582) and another group having MR-proANP values below the optimum threshold-level (FIG. 14).

The optimum threshold levels identified in the present invention are based on the particular population investigated, and they might be different (+/−20%) in other comparable populations due to reasons described above.

In the context of the present invention, the terms "threshold", "threshold value", "cut-off" and "cut-off value" are used synonymously.

These results are further supported by Cox regression analysis (Table 4) demonstrating the use of both MR-proANP and MR-proADM for prediction of the progression of primary chronic kidney disease (CKD).

Other mathematical possibilities to calculate an individual's risk by using the individual's MR-proADM and/or MR-proANP value and other prognostic laboratory and clinical parameters are for instance the NRI (Net Reclassification Index) or the IDI (Integrated Discrimination Index). The indices can be calculated according to Pencina (Pencina M J, et al.: Evaluating the added predictive ability of a new marker: from area under the ROC curve to reclassification and beyond. Stat Med. 2008; 27: 157-172).

In certain embodiments, particular thresholds for one or more markers in a panel are not relied upon to determine if a profile of marker levels obtained from a subject are indicative of a particular diagnosis/prognosis. Rather, the present invention may utilize an evaluation of a marker panel "profile" as a unitary whole. A particular "fingerprint" pattern of changes in such a panel of markers may, in effect, act as a specific diagnostic or prognostic indicator. As discussed herein, that pattern of changes may be obtained from a single sample, or from temporal changes in one or more members of the panel (or a panel response value). A panel herein refers to a set of markers.

A panel response value can be derived by various methods. One example is Cox proportional hazards analysis. Another example is optimizing ROC curves: This can be achieved by plotting ROC curves for the sensitivity of a particular panel of markers versus 1-(specificity) for the panel at various cut-offs.

In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the method according to the invention said sample is selected from the group comprising a blood sample, a serum sample, a plasma sample, and a urine sample or an extract of any of the aforementioned samples.

The term "patient" as used herein refers to a living human or non-human organism that is receiving medical care or that should receive medical care due to a disease. This includes persons with no defined illness who are being investigated for signs of pathology. Thus, the methods and assays described herein are applicable to both human and veterinary disease.

The term "correlating," as used herein in reference to the use of diagnostic and prognostic markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels are correlated to a global probability or a particular outcome.

A "prognosis" refers to assignment of a probability that a given course or outcome will occur. This is often determined by examining one or more "prognostic indicators". These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for eventually advancing into end-stage renal disease (ESRD), i.e. the patient has an increased probability of being a "progressor".

In a preferred embodiment of the invention the level of MR-proADM is measured. MR-proADM comprises amino acids 45-92 of pre-proADM.

In another preferred embodiment of the invention the level of proADM or fragments thereof is measured using a diagnostic assay using one or more capture probes directed against one ore more epitopes located in amino acid positions 45-92 of pre-proADM.

In another preferred embodiment of the invention the level of MR-proANP is measured. MR-proANP means any fragments of proANP comprising amino acids 53-90 of proANP.

In another preferred embodiment of the invention the level of proANP or fragments thereof is measured using a diagnostic assay using one or more capture probes directed against one ore more epitopes located in amino acid positions 53-90 of proANP.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

The level of the above-mentioned markers can be obtained by any art recognized method. Typically, the level is determined by measuring the level or activity of the marker in a body fluid, for example, blood, lymph, saliva, urine and the like. The level can be determined by immunoassays or other conventional techniques for determining the level of the marker. Recognized methods include sending samples of a patient's body fluid to a commercial laboratory for measurement, but also performing the measurement at the point-of-care.

In the context of the present invention, "capture molecules" are molecules which may be used to bind target molecules or molecules of interest, i.e. analytes, from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a PNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassays, chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competive sandwich assays. In a particularly preferred embodiment, the assay is in the form of a sandwich assay, which is a noncompetitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 Feb.; 10(1): 4-10. PMID: 16376134), incorporated herein by reference.

In a particularly preferred embodiment the assay comprises two capture molecules, preferably antibodies which are both present as dispersions in a liquid reaction mixture, wherein a first marking component is attached to the first capture molecule, wherein said first marking component is part of a marking system based on fluorescence- or chemiluminescence-quenching or amplification, and a second marking component of said marking system is attached to the second capture molecule, so that upon binding of both capture molecules to the analyte a measurable signal is generated that allows for the detection of the formed sandwich complexes in the solution comprising the sample.

Even more preferred, said marking system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), RHODAMINE, RHODAMINE GREEN, RHODAMINE RED, RHODAMINE 110, BODIPY dyes, such as BODIPY TMR, Oregon Green, Coumarines such as Umbelliferone, Benzimides, such as Hoechst 33258; Phenanthridines, such as TEXAS RED, YAKIMA YELLOW, ALEXA FLUOR, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are Acridiniumesters.

In an especially preferred embodiment a MR-proADM assay is used having a detection limit below 0.3 nmol/L and an interassay precision of <30% CV in the normal range for predicting a first adverse event in a subject or identifying a subject having an enhanced risk for getting a first adverse event.

Another embodiment of the present invention is the use of a capture probe, e.g. antibody directed against proADM or fragments thereof for predicting a first adverse event in a subject or identifying a subject having an enhanced risk for getting a first adverse event.

Especially preferred in the context of the present invention is the use of one or more antibodies which are directed against an epitope included in the amino acids positions 45-92 of pre-proADM and/or against an epitope included in the amino acids positions 53-90 of proANP.

EXAMPLES

Example 1

Mild to Moderate Kidney Disease (MMKD) Study

The aim of the present study was to investigate the predictive value of ANP and ADM, using novel sandwich immunoassays covering the midregional epitopes of the more stable prohormone fragments (MR-proANP and MR-proADM), for kidney disease progression in a prospective 7-year follow up study in a cohort of patients with primary CKD.

Results

Table 1 shows NT-proBNP, MR-proANP, and MR-proADM plasma concentrations at baseline GFR stratified in stages according to the K/DOQI clinical practice guidelines for chronic kidney disease. There was a continuous increase of median NT-proBNP, MR-proANP, and MR-proADM plasma concentrations across the CKD stages. Furthermore, nonparametric correlation analyses revealed significant associations between GFR and all three parameters (Table 2).

Follow-up was available in 177 out of the 227 enrolled patients. The median duration of follow-up after completion of the baseline investigation was 53 months (range 3 to 84 months). During follow-up 65 patients progressed to the endpoint which was doubling of serum creatinine without reaching ESRD in 36 patients and ESRD requiring renal replacement therapy in 29 patients. Table 3 reports the baseline CKD patient characteristics for the progressors and non-progressors. Patients who reached the progression endpoint were older, had higher protein excretion rates as well as lower GFR. In addition median plasma concentrations of NT-proBNP, MR-proANP, and MR-proADM were higher in the progressors than in non-progressors (NT-proBNP, 321 vs. 84 ng/L; MR-proANP, 164 vs. 74 pmol/L; and MR-proADM, 1.13 vs. 0.55 nmol/L).

Kaplan-Meier curve analyses of the 177 patients with CKD who were stratified into two groups according to the median of MR-proANP, and MR-proADM at baseline are shown in FIGS. 11 to 12. Patients who had GFR values below the median and MR-proANP and MR-proADM plasma concentrations above the median had a worse renal prognosis and significant shorter progression time compared with patients with GFR values above the median and MR-proANP and MR-proADM plasma concentrations below the median [mean time to progression in months was 51.1 (95% CI 45.2-57.1) vs. 71.4 (95% CI 64.7-78.1), p<0.001 for MR-proANP; and 51.6 (95% CI 45.6-57.6) vs. 73.6 (95% CI 68.5-78.6), p<0.001 for MRproADM, respectively]. Univariate Cox proportional-hazards regression analyses using the approach of stratifying the predictor variables according to the median values revealed significantly decreased hazard ratios (HRs) for GFR above the median (HR 0.12; 95% CI 0.06-0.24; p<0.001) and significantly increased HRs for concentrations above the median at baseline for NT-proBNP (HR 3.84; 95% CI 2.14-6.89; p<0.001), MR-proANP (HR 4.47; 95% CI 2.46-8.12; p<0.001), and MR-proADM (HR 5.84; 95% CI 3.04-11.21; p<0.001).

The results of Cox proportional-hazards regression analyses using an incremental approach for the predictor variables are given in Table 4. In the age- and sex-adjusted Model 1 GFR, proteinuria, NT-proBNP, MR-proANP, and MR-proADM revealed significant HR for kidney disease progression. After further adjustment for GRF and proteinuria, the HR for MR-proANP and MR-proADM where slightly attenuated but both variables remained strongly associated with disease progression, whereas the HR for NT-proBNP was no longer significant (Model 2). Even after additional adjustment for NT-proBNP both, MR-proANP and MR-proADM, each remained a strong predictor of kidney disease progression (Model 3). Since several of the investigated variables were non-normally distributed we performed a sensitivity analysis by including the ln-transformed variables into the model. These analyses revealed very similar results (data not shown) with the exception of NT-proBNP which remained significant after adjustment for age, sex, GFR and proteinuria (HR 1.59; 95% CI 1.15-2.19; p=0.005). For a better interpretability of the estimates, however, we present data on the original scale.

We furthermore investigated whether both, MR-proANP and MR-proADM, independently add to the prediction of CKD progression by including both variables in the same Cox regression model and adjusting for age, sex, GFR and proteinuria. The hazard ratios of both variables decreased (compared to the estimates in Model 2 of Table 4) but still remained significant (HR 1.60; 95% CI 1.11-2.30, p=0.011 for MR-proANP and HR 1.96; 95% CI 1.31-2.94, p<0.001 for MR-proADM).

In a secondary analysis we included only patients in stage 3 and higher according to K/DOQI clinical practice guidelines for chronic kidney disease (GFR <60 ml/min/1.73 m$^2$). We observed very similar estimates as presented for Model 2 and 3 of Table 4 for the entire group (data not shown).

Discussion

The present study is the first prospective long-term observation investigating the prognostic value of MR-proANP and MR-proADM for renal disease progression in Caucasian patients with primary CKD. Our data indicate that increased MR-proANP and MR-proADM plasma concentrations at baseline are strong predictors of renal endpoints which are even independent from GFR.

Through the adoption of the K/DOQI recommendations and routinely reported estimates of GFR by many laboratories, substantial success has been achieved in screening for undiagnosed CKD (National Kidney Foundation. Am J Kidney Dis 2002; 39 (2 Suppl 1): S1-266; Centers for Disease Control and Prevention (CDC), Morb Mortal Wkly Rep 2007; 56: 161-165). However, there is an urgent need for further risk stratification and the identification of further risk predictors to target interventions to those patients with CKD most likely to progress to ESRD.

An important finding of our study was the fact that MR-proANP and MR-proADM were strongly correlated with GFR measured by iohexol, which has been reported to come close to the gold standard of measuring kidney function (Bostom et al., J Am Soc Nephrol 2002; 13: 2140-2144). We observed a continuous increase in MR-proANP and MR-proADM plasma concentrations across GFR stages, indicating an association with disease severity. This strong correlation with GFR may be attributable to the evidence that ANP and ADM are produced in the kidney (Vesely et al., Am J Physiol Renal Physiol 2003; 285: 167-177), and both have important biological functions within the kidney (Vesely et al, Cardiovasc Res 2001; 51: 647-658; Nishikimi et al., Curr Med Chem 2007; 14: 1689-1699). Furthermore, renoprotective properties for both peptides have been reported, suggesting a compensatory role of increased concentrations of ANP and ADM in CKD (Vesely et al., Cardiovasc Res 2001; 51: 647-658; Vesely et al., Am J Physiol Renal Physiol 2003; 285: 167-177; Nishikimi et al., Curr Med Chem 2007; 14: 1689-1699).

In the setting evaluated, the prognostic values of MR-proANP and MR-proADM were comparable with that of GFR, an established prognostic, but difficult to determine marker in kidney disease progression. In the age- and sex-adjusted Cox-proportional hazard regression models the behavior of GFR, MR-proANP, and MR-proADM was similar. However, it is important to note that besides GFR both, MR-proANP and MR-proADM, added significantly to the prediction of disease progression. An increase of each of both parameters by one standard deviation was associated with more than twice the risk of disease progression even after adjustment for baseline GFR. Even if we added both parameters at the same time to the model resulted in a significant and independent contribution of both parameters to the risk prediction.

The prognostic ability of NT-proBNP was lower compared with GFR, MR-proANP or MR-proADM.

It is important to note that GFR in our study was not calculated by a formula but was measured by iohexol clearance which is considered an exact method to measure kidney function. This method, however, is laborious and is a burden for the patient due to the application of contrast media and the collection of several blood samples. Measurement of MR-proANP or MR-proADM is an alternative and simple method which provides a good approximation of kidney function and a well performing predictor for the progression of kidney disease which performs equal to GFR.

In summary, our work demonstrates that increased MR-proANP and MR-proADM plasma concentrations at baseline are powerful predictors of progression of kidney disease. Therefore, both markers are clinically useful as predictors in patients with primary CKD.

Concise Methods

Study Sample

At baseline 227 Caucasian patients aged between 18 and 65 years with CKD and various degrees of renal impairment were enrolled into the Mild to Moderate Kidney Disease (MMKD) study. These patients were recruited from 8 nephrology departments as described in Kronenberg et al. (J Am Soc Nephrol 2000; 11: 105-115). This study was approved by the Institutional Ethic Committees, and all subjects gave written informed consent. They had stable renal function for at least 3 months before entry into the study. Exclusion criteria were treatment with immunosuppressive agents, fish oil or erythropoietin, serum creatinine above 6 mg/dL, diabetes mellitus of any type, malignancy, liver, thyroid or infectious disease, nephrotic syndrome (defined as proteinuria >3.5 g/1.73 m$^2$/day), organ transplantation, allergy to ionic contrast media and pregnancy. In order to avoid inter-observer differences, all patients were recruited by one physician who visited all participating centers. Patient history, including smoking habits and antihypertensive treatment at baseline was recorded by interview and confirmed by checking patient records. This was complemented by clinical examination including assessment of body mass index and blood pressure. Hypertension was defined as blood pressure above 140/90 mm Hg and/or the use of antihypertensive medication. Antihypertensive medication was withheld on the day of study enrollment in order to minimize interference with measurements of GFR. Antihypertensive drugs were taken by 179 patients (79%): diuretics (n=83; 37%), ACE-inhibitors (n=123; 54%), calcium channel blockers (n=78; 34%), beta receptor blockers (n=67; 30%) and alpha-1 receptor blockers (n=36; 16%).

The primary cause of kidney disease was glomerulonephritis in 97 (biopsy-confirmed in 90) patients, adult polycystic kidney disease in 37 patients, interstitial nephritis in 24 patients, other types of kidney disease in 43 patients and unknown in 26 patients. The distribution of patients over the stages of CKD according to the K/DOQI clinical practice guidelines for chronic kidney disease classification[2] is provided in Table 1.

The endpoint of the follow-up investigation was defined as doubling of baseline serum creatinine and/or ESRD necessitating renal replacement therapy. Of the primary cohort of 227 patients, 177 patients (78%) were followed prospectively over a period of up to 84 months (Boes et al. J Am Soc Nephrol 2006; 17: 528-536). Patients were under regular control in the outpatient ward and endpoints were reported to the study coordinating center. Patients, who were lost during follow-up, had moved home or were not referred to the study centers after baseline investigation. Compared to patients with follow-up, these patients had significantly better renal function at baseline but did not differ significantly in gender and age.

Biochemical Analysis

Blood samples were drawn after an overnight fast of at least 12 hours. The samples were immediately centrifuged at 1.500 g and 4° C. for 10 minutes, and the supernatants stored in aliquots at −80° C. until further use. GFR was assessed in patients using the iohexol clearance technique as described in detail in Bostom et al. (J Am Soc Nephrol 2002; 13: 2140-2144). Routine biochemical analyses, including serum ceatinine, proteiunria, serum albumin, and high-sensitivity C-reactive protein, were performed as described in Kronenberg et al. (J Am Soc Nephrol 2000; 11: 105-115). Plasma NT-proBNP was measured on a Modular Analytics E170 System (Roche Diagnostics, Mannheim, Germany) (Spanaus et al., Clin Chem 2007; 53: 1264-1272). MR-proANP and MR-proADM plasma concentrations were measured by commercially available immunoluminometric assays (B.R.A.H.M.S. AG, Hennigsdorf Germany). The precision of these two methods has been evaluated and described previously (Morgenthaler et al., Clin Chem 2004; 50: 234-236; Morgenthaler et al., Clin Chem 2005; 51: 1823-1829.).

Statistical Analysis

Statistical analysis was performed using the SPSS version 13.0 software (SPSS Inc., Chicago, Ill., USA), and the MedCalc 9.4.2.0 package (MedCalc Software, Mariakerke, Belgium). Univariate comparisons of continuous variables between various groups were performed using one-way ANOVA, unpaired t-test or the nonparametric Kruskal-Wallis or Wilcoxon rank sum test in case of non-normally distributed variables. Dichotomized variables were compared using Pearson's $\chi^2$-test. Data are presented as mean±standard deviation (SD) and as median and $25^{th}$ and $75^{th}$ percentile for skewed variables where appropriate. The Spearman coefficient of rank correlation ($r_s$) was used to assess the relationship between the four main study parameters (i.e., GFR, NT-proBNP, MR-proANP, and MR-proADM). Kaplan-Meier estimates of the distribution of times from baseline to renal endpoints were generated, for patients with GFR, NT-proBNP, MR-proANP, and MR-proADM above and below the median value of the entire study population; logrank tests were calculated to compare the survival curves between the groups. Univariate Cox proportional-hazards regression analysis was performed, with all four parameters dichotomized according to the median concentration of the entire cohort. In addition, adjusted risk estimates for progression endpoints were calculated using an incremental approach for each increment of 1 standard deviation (SD) of the respective data. All probabilities were two for that-tailed and P values <0.05 were regarded as significant.

TABLE 1

Baseline clinical and laboratory data of 227 patients stratified according to glomerular filtration rate (GFR) in National Kidney Foundation stages

| | GFR mL/min/1.73 m² | | | | |
|---|---|---|---|---|---|
| | >=90 (n = 72) | 60-89 (n = 49) | 30-59 (n = 63) | <30 (n = 43) | p-value* |
| Gender (male/female), n (%) | 50/22 (69.4/30.6) | 34/15 (69.4/30.6) | 44/19 (68.8/30.2) | 26/17 (60.5/39.5) | 0.72 |
| Age (years) | 39.9 ± 13.2 | 46.1 ± 11.6 | 45.9 ± 11.5 | 54.4 ± 8.5 | <0.001 |
| Body mass index (kg/m²) | 24.0 ± 3.3 | 25.6 ± 3.8 | 25.4 ± 3.4 | 26.1 ± 4.8 | 0.02 |
| Current smokers, n (%) | 18 (25) | 11 (22) | 11 (18) | 9 (21) | 0.97 |
| Systolic blood pressure (mmHg) | 134 ± 21 | 140 ± 24 | 139 ± 19 | 137 ± 19 | 0.21 |
| Diastolic blood pressure (mmHg) | 84 ± 13 | 88 ± 15 | 88 ± 14 | 88 ± 13 | 0.20 |
| Serum creatinine (mg/dL) | 1.14 ± 0.22 [0.95; 1.11; 1.30] | 1.54 ± 0.45 [1.25; 1.43; 1.70] | 2.31 ± 0.79 [1.70; 2.18; 2.80] | 3.63 ± 1.28 [2.73; 3.50; 4.61] | <0.001 |
| GFR (mL/min/1.73 m²) | 120 ± 28 [97; 110; 132] | 74 ± 9 [65; 71; 81] | 44 ± 7 [38; 44; 50] | 19 ± 7 [12; 18; 26] | <0.001 |
| Proteinuria (g/24 h/1.73 m²) | 0.60 ± 0.66 [0.13; 0.36; 0.82] | 1.10 ± 1.10 [0.16; 0.57; 1.93] | 1.08 ± 0.94 [0.27; 0.81; 1.83] | 1.03 ± 0.81 [0.36; 0.89; 1.52] | 0.004 |
| Serum albumin (g/dL) | 4.70 ± 0.38 | 4.46 ± 0.50 | 4.55 ± 0.38 | 4.53 ± 0.34 | 0.01 |
| High sensitivity C-reactive protein (mg/L) | 0.21 ± 0.27 [0.04; 0.09; 0.23] | 0.32 ± 0.33 [0.13; 0.21; 0.42] | 0.23 ± 0.21 [0.06; 0.14; 0.36] | 0.35 ± 0.38 [0.08; 0.18; 0.53] | 0.01 |
| NT-proBNP (ng/L)† | 64 ± 76 [22; 39; 76] | 180 ± 221 [45; 91; 199] | 380 ± 616 [78; 173; 409] | 769 ± 846 [232; 456; 1002] | <0.001 |

TABLE 1-continued

Baseline clinical and laboratory data of 227 patients stratified according to glomerular filtration rate (GFR) in National Kidney Foundation stages

| | GFR mL/min/1.73 m² | | | | |
|---|---|---|---|---|---|
| | >=90 (n = 72) | 60-89 (n = 49) | 30-59 (n = 63) | <30 (n = 43) | p-value* |
| MR-proANP (pmol/L)† | 56 ± 28 [37; 49; 68] | 95 ± 49 [60; 78; 120] | 159 ± 123 [82; 130; 193] | 279 ± 161 [168; 248; 339] | <0.001 |
| MR-proADM (nmol/L)† | 0.43 ± 0.12 [0.33; 0.42; 0.49] | 0.65 ± 0.20 [0.50; 0.63; 0.78] | 0.90 ± 0.30 [0.69; 0.89; 1.01] | 1.34 ± 0.39 [1.15; 1.28; 1.52] | <0.001 |

Abbreviations: GFR, glomerular filtration rate; MR-proADM, mid-regional pro-adrenomedullin; MR-proANP, mid-regional pro-A-type natriuretic peptide; NT-proBNP, amino terminal pro B-type natriuretic peptide.
*P-values are for comparison across all 4 groups obtained from Kruskal-Wallis test, one-way ANOVA, and chi-square test, where appropriate.
Data are presented as mean ± SD and $25^{th}$, $50^{th}$ (= median), $75^{th}$ percentile for skewed variables where appropriate.
†Plasma levels of NT-proBNP, MR-proANP and MR-proADM were available in 222, 221, and 220 of the 227 patients, respectively.

TABLE 2

Spearman correlation coefficient (p-value) between the variables GFR, NT-proBNP, MR-proANP, and MR-proADM plasma concentrations in the 227 patients enrolled at baseline

| | NT-proBNP | MR-proANP | MR-proADM |
|---|---|---|---|
| GFR | −0.609 (<0.001) | −0.705 (<0.001) | −0.815 (<0.001) |
| NT-proBNP | | 0.888 (<0.001) | 0.737 (<0.001) |
| MR-proANP | | | 0.845 (<0.001) |

Abbreviations: GFR, glomerular filtration rate; MR-proADM, mid-regional pro-adrenomedullin; MR-proANP, mid-regional pro-A-type natriuretic peptide; NT-proBNP, amino terminal pro B-type natriuretic peptide.

TABLE 3

Baseline clinical and laboratory data of 177 patients with completed follow-up with further stratification of those with and without progression of kidney disease during the follow-up period

| | Non-Progressors (n = 112) | Progressors (n = 65) | p-value |
|---|---|---|---|
| Gender (male/female), n (%) | 74/38 (66/34) | 44/21 (68/32) | 0.83 |
| Age (years) | 44.8 ± 12.6 | 49.1 ± 11.1 | 0.03 |
| Body mass index (kg/m²) | 24.9 ± 3.5 | 25.7 ± 3.9 | 0.13 |
| Current smokers, n (%) | 18 (16) | 16 (25) | 0.21 |
| Systolic blood pressure (mmHg) | 136 ± 22 | 137 ± 17 | 0.72 |
| Diastolic blood pressure (mmHg) | 86 ± 14 | 88 ± 12 | 0.34 |
| Serum creatinine (mg/dL) | 1.54 ± 0.61 [1.14; 1.40; 1.80] | 3.21 ± 1.31 [2.21; 3.10; 3.94] | <0.001 |
| Glomerular filtration rate (mL/min/1.73 m²) | 79 ± 38 [50; 74; 99] | 38 ± 25 [20; 33; 46] | <0.001 |
| Proteinuria (g/24 h/1.73 m²) | 0.87 ± 0.95 [0.14; 0.46; 1.25] | 1.25 ± 0.83 [0.61; 1.09; 1.78] | <0.001 |
| Serum albumin (g/dL) | 4.57 ± 0.43 | 4.53 ± 0.36 | 0.50 |
| High sensitivity C-reactive protein (mg/L) | 0.28 ± 0.32 [0.07; 0.17; 0.39] | 0.29 ± 0.31 [0.08; 0.16; 0.43] | 0.59 |
| NT-proBNP (ng/L)* | 182 ± 305 [44; 84; 176] | 579 ± 717 [117; 321; 745] | <0.001 |
| proANP (pmol/L)* | 97 ± 66 [48; 74; 128] | 225 ± 171 [111; 164; 274] | <0.001 |
| proADM (nmol/L)* | 0.63 ± 0.28 [0.43; 0.55; 0.79] | 1.15 ± 0.42 [0.91; 1.13; 1.36] | <0.001 |

Abbreviations: GFR, glomerular filtration rate; MR-proADM, mid-regional pro-adrenomedullin; MR-proANP, mid-regional pro-A-type natriuretic peptide; NT-proBNP, amino terminal pro B-type natriuretic peptide.
Data are presented as mean ± SD and $25^{th}$, $50^{th}$ (= median), $75^{th}$ percentile for skewed variables where appropriate.
*Plasma levels of NT-proBNP, MR-proANP and MR-proADM were available in 174, 174, and 173 of the 177 patients, respectively.

TABLE 4

The association of baseline variables with progression of kidney disease during the observation period using multiple Cox proportional hazards regression models

| Variable (increment) | Model 1 Adjusted for age and sex | | Model 2 Adjusted for age, sex GFR, and proteinuria | | Model 3 Adjusted for age, sex, GFR, proteinuria, and NT-proBNP | |
|---|---|---|---|---|---|---|
| | HR (95% CI) | p | HR (95% CI) | p | HR (95% CI) | p |
| GFR (per 1 SD increase)* | 0.21 (0.13-0.34) | <0.001 | — | | — | |
| Proteinuria (per 1 SD increase)† | 1.27 (1.02-1.58) | 0.032 | — | | — | |
| NT-proBNP (per 1 SD increase)‡ | 1.45 (1.24-1.69) | <0.001 | 1.15 (0.96-1.38)# | 0.127 | — | |
| MR-proANP (per 1 SD increase)§ | 2.88 (2.25-3.68) | <0.001 | 2.11 (1.59-2.80)# | <0.001 | 2.90 (1.94-4.34)## | <0.001 |

TABLE 4-continued

The association of baseline variables with progression of kidney
disease during the observation period using multiple Cox proportional
hazards regression models

| Variable (increment) | Model 1 Adjusted for age and sex | | Model 2 Adjusted for age, sex GFR, and proteinuria | | Model 3 Adjusted for age, sex, GFR, proteinuria, and NT-proBNP | |
|---|---|---|---|---|---|---|
| | HR (95% CI) | p | HR (95% CI) | p | HR (95% CI) | p |
| MR-proADM (per 1 SD increase)¶ | 3.41 (2.61-4.45) | <0.001 | 2.60 (1.85-3.64)# | <0.001 | 2.62 (1.84-3.74)## | <0.001 |

Abbreviations:
GFR, glomerular filtration rate;
MR-proANP, mid-regional pro-A-type natriuretic peptide;
MR-proADM, mid-regional pro-adrenomedullin,
NT-proBNP, amino terminal pro B-type natriuretic peptide.
*For GFR 1 SD increment was 39 mL/min/1.73 m$^2$,
†for proteinuria it was 0.92 g/24 h/1.73 m$^2$,
‡for NT-proBNP it was 527 ng/L, for
§MR-proANP it was 131 pmol/L, and
¶for MR-proADM it was 0.42 nmol/L, respectively.
MR-proANP, MR-proADM, and NT-proBNP were not included at the same time, but were adjusted for the same variables: age, sex, GFR, proteinuria.
MR-proANP and MR-proADM were not included at the same time, but were adjusted for the same variables: age, sex, GFR, proteinuria, and NT-proBNP.

DESCRIPTION OF DRAWINGS

FIG. 1: Amino acid sequence of the adrenomedullin (ADM) precursor peptide (pre-pro-ADM). Amino acids 1-21 form a signal peptide. Amino acids 22-41 form the pro-ADM N-20 terminal peptide (proADM N20). Amino acids 45-92 form the MR-proADM peptide. Mature ADM comprises amino acids 95-146. Amino acids 148-185 form the proADM C-terminal fragment.

FIG. 2: Amino acid sequence of the pro-adrenomedullin peptide (proADM).

FIG. 3: Amino acid sequence of the pro-adrenomedullin N-terminal 20 peptide (proADM N20; PAMP). The PAMP peptide may have an amidated C-term.

FIG. 4: Amino acid sequence of the MR pro-adrenomedullin (MR-proADM).

FIG. 5: Amino acid sequence of the mature adrenomedullin peptide (ADM). ADM peptide may have an amidated C-term and/or may be glycosylated.

FIG. 6: Amino acid sequence of the artrial natriuretic peptide (ANP) precursor (pre-pro-ANP). Amino acids 1-25 form a signal peptide.

FIG. 7: Amino acid sequence of the proANP.

FIG. 8: Amino acid sequence of mature ANP.

FIG. 9: Amino acid sequence of NT-proANP.

FIG. 10: Amino acid sequence of amino acids 53 to 90 of proANP.

Figure 11:
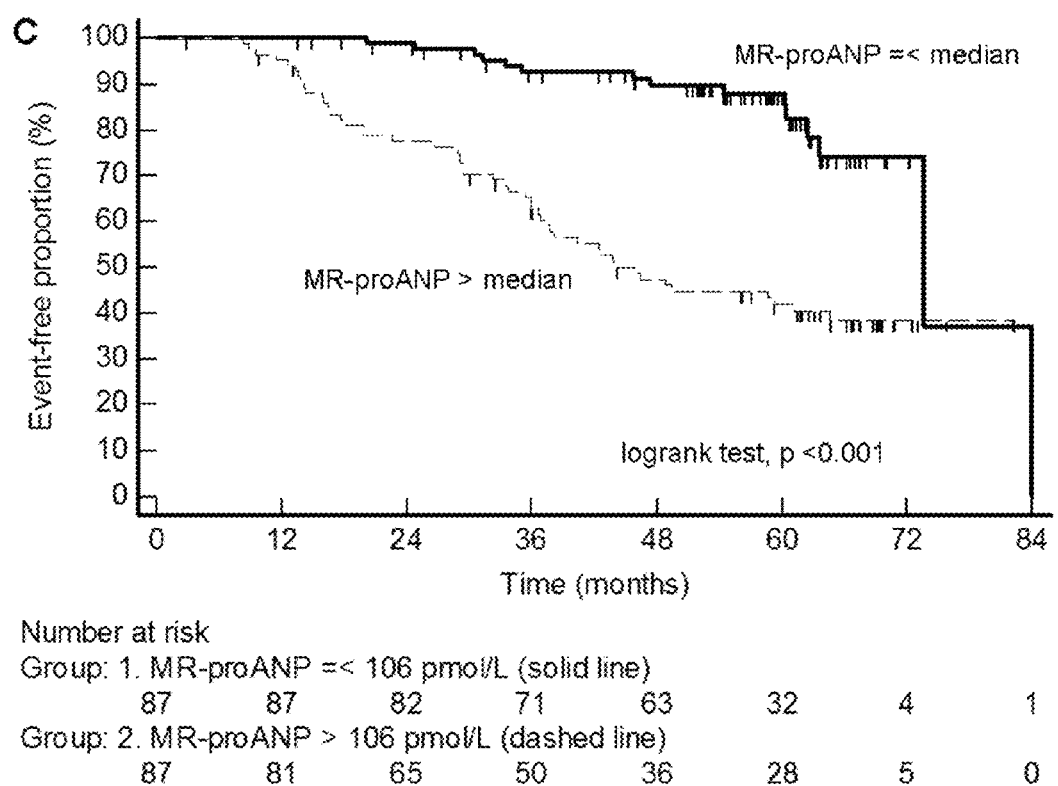
FIG. 11: Kaplan-Meier plots showing renal disease progression in patients with CKD who were stratified into two groups according to the medians of MR-proANP (106 pmol/L) at baseline.
Figure 12:
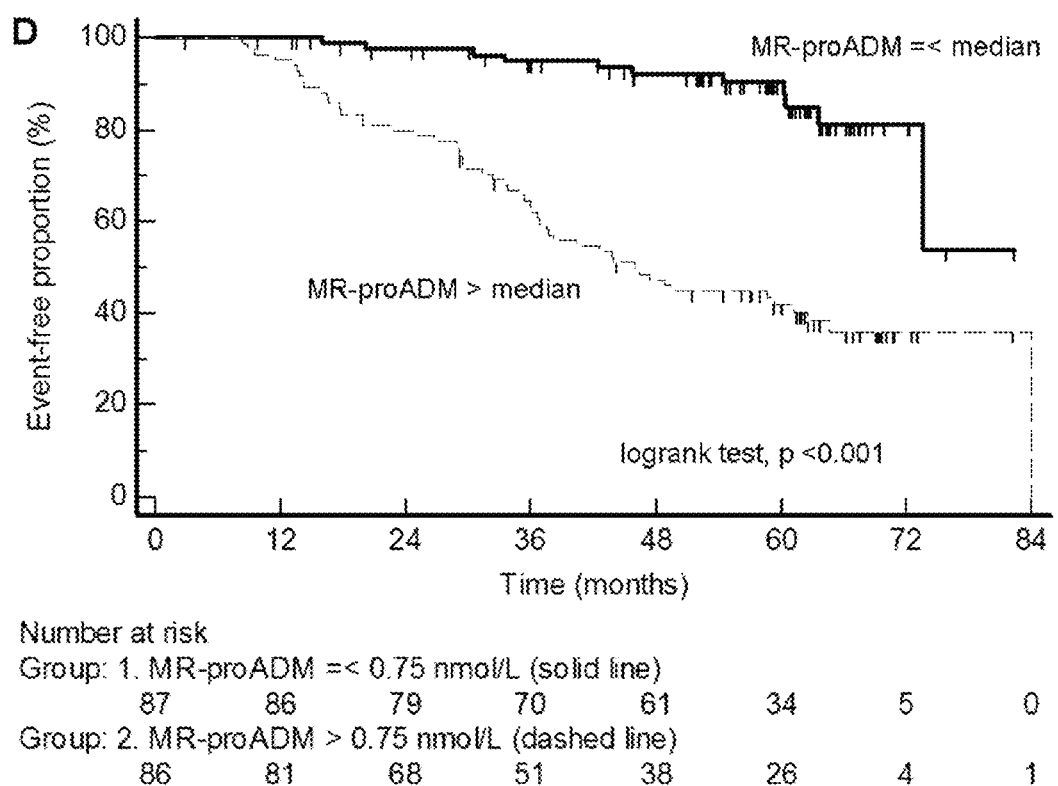
FIG. 12: Kaplan-Meier plots showing renal disease progression in patients with CKD who were stratified into two groups according to the medians of MR-proADM (0.75 nmol/L) at baseline.
Figure 13:
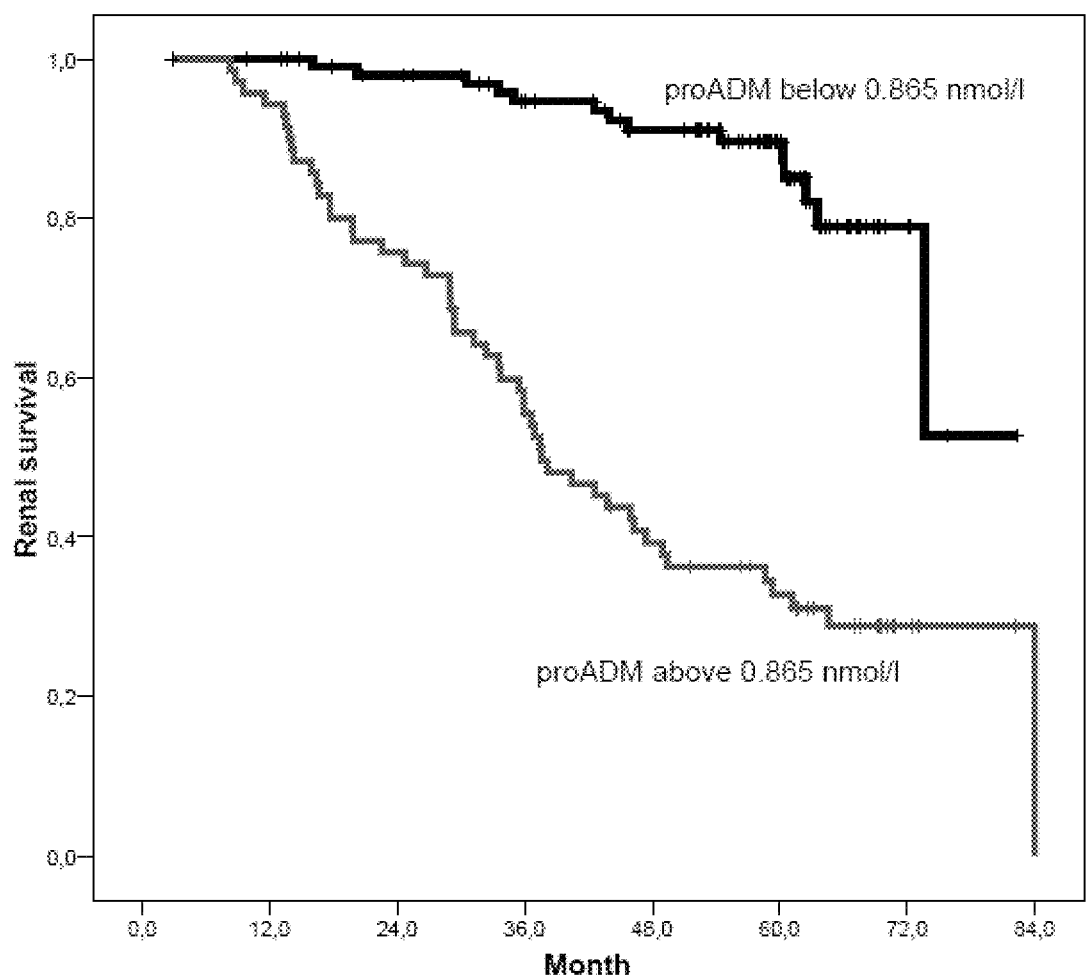
FIG. 13: Kaplan Meier curve with optimal cut-off for MR-proADM: Sensitivity=0.766, specificity=0.809, logrank: p=<0.001.
Figure 14:
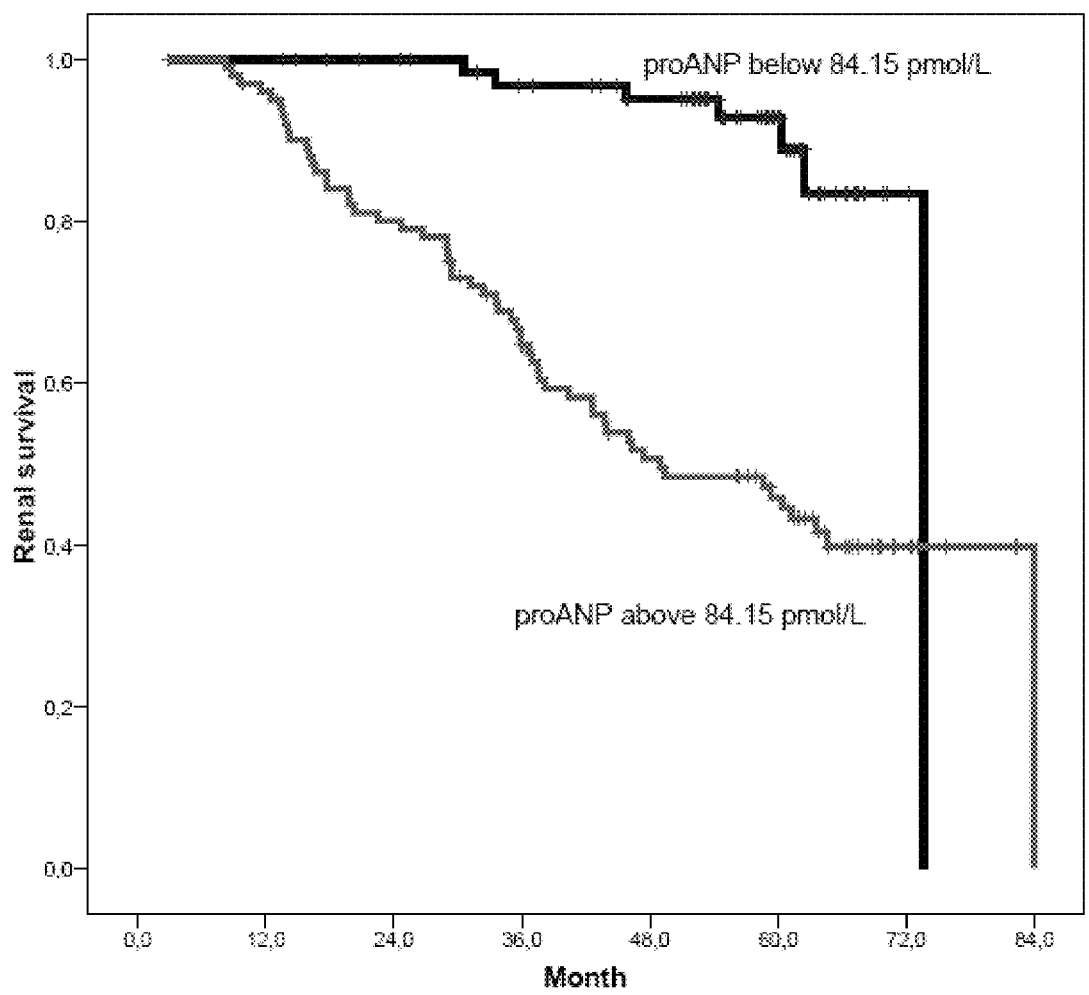
FIG. 14: Kaplan Meier curve with optimal cut-off for MR-proANP: Sensitivity (0.891), specificity=0.582, logrank: p=<0.001.

The invention claimed is:

1. A method for prediction of the progression of primary chronic kidney disease or for monitoring chronic kidney disease therapy, comprising:
   a. detecting and quantitating the level of one or more markers selected from the group consisting of MR-proADM of SEQ ID NO:4 and/or MR-proANP of SEQ ID NO:10 in a sample from a patient suffering from chronic kidney disease, wherein said detection and quantitation comprises contact the sample with a diagnostic assay reagent comprising a capture probe that specifically binds to MR-proADM or MR-proANP, respectively, and detecting and quantitating thus-formed complexes of capture probe and MR-proADM and/or MR-proANP,
   b. predicting the progression of primary chronic kidney disease or monitoring chronic kidney disease therapy by comparing the level of MR-proADM and/or MR-proANP in the patient to a predetermined statistically significant cutoff level of MR-proADM and/or MR-proANP in an ensemble of pre-determined samples in a population of primary chronic kidney disease patients whose chronic kidney disease progressed (progressor) or did not progress (non-progressor), with or without said therapy, wherein said prediction is based on a statistically significant correlation of the level of MR-proADM and/or MR-proANP with the levels of the marker in the pre-determined samples.

2. The method of claim 1, whereby said patient is classified as a progressor or a non-progressor.

3. The method of claim 1, wherein the level of MR-proANP is quantitated and used as single marker.

4. The method of claim 1, wherein the level of MR-proADM is determined and used as single marker.

5. The method of claim 1, wherein the prediction of the progression of primary chronic kidney disease is improved by additionally
   c. detecting and quantitating the level of at least one laboratory parameter or further marker selected from the group consisting of: creatinine, glomerular filtration rate (GFR), Proteinuria, albumin, C-reactive protein (CRP), Cystatin C, growth differentiation factor 15 (GDF15), interleukin 1 receptor-like 1 (ST2), Neutrophil Gelatinase-Associated Lipocalin (NGAL), Procalcitonin, type-B natriuretic peptide (BNP), or a precursor or fragment thereof selected from proBNP or NT-proBNP, pro-Vasopressin and fragments thereof selected from copeptin, vasopressin or neurophysin II, pro-Endothelin-1 and fragments thereof selected from CT-proET-1, NT-proET-1, big-Endothelin-1 or Endothelin-1; wherein said detection and quantitation of the further markers selected from the group consisting of creatinine, GFR, Proteinuria, albumin, CRP, Cystatin C, BNP or a precursor or fragment thereof selected from proBNP or NT-proBNP, GDF15, ST2, NGAL, procalcitonin, pro-Vasopressin and fragments thereof selected from copeptin, vasopressin or neurophysin II, and pro-Endothelin-1 and fragments thereof selected from CT-proET-1, NT-proET-1, big-Endothelin-1 or Endothelin-1, comprises contacting the sample with a diagnostic assay reagent comprising a capture probe that specifically binds to said further marker, and detecting and quantitating thus-formed complexes of capture probe and further marker, and
   d. improving the prediction of the risk of progression of chronic kidney disease in said subject by comparing the level of each of said laboratory parameters or markers in the patient to a predetermined statistically significant cutoff level of each of said laboratory parameters or markers in an ensemble of pre-determined samples in a population of primary chronic kidney disease patients whose primary chronic kidney disease progressed (progressor) or did not progress (non-progressor), wherein said prediction is based on a statistically significant correlation of the levels of the laboratory parameters or markers in the patient sample with the levels of the laboratory parameters or markers in the pre-determined samples.

6. The method of claim 1, wherein additionally at least one clinical parameter is determined selected from the group consisting of: age, gender, systolic blood pressure, diastolic blood pressure, antihypertensive treatment, body mass index, and smoking habits.

7. The method for prediction of the progression of primary chronic kidney disease and for monitoring the chronic kidney disease therapy of claim 1, wherein the predetermined statistically significant cutoff level of MR-proADM and/or MR-proANP either alone or in conjunction with other prognostically useful laboratory or clinical parameters is determined by a method selected from the following alternatives:
   i. Comparison with the median of the level of MR-proADM and/or MR-proANP in an ensemble of pre-determined samples in a population of primary chronic kidney disease patients,
   ii. Comparison with a quantile of the level of MR-proADM and/or MR-proANP in an ensemble of pre-determined samples in a population of primary chronic kidney disease patients,
   iii. Calculation based on Cox Proportional Hazards analysis or by using Risk index calculations such as the NRI (Net Reclassification Index) or the IDI (Integrated Discrimination Index).

8. The method of claim 1, wherein the level of MR-proADM is measured using a diagnostic assay comprising one or more capture probes directed against one or more epitopes located in amino acid positions 45-92 of pre-proADM.

9. A method for predicting renal endpoints in a patient suffering from primary chronic kidney disease comprising
   a. detecting and quantitating the level of one or more markers selected from the group consisting of MR-proADM of SEQ ID NO:4 and/or MR-proANP of SEQ ID NO:10 in a sample from said patient, wherein said detection and quantitation comprises contact the sample with a diagnostic assay reagent comprising a capture probe that specifically binds to MR-proADM or MR-proANP, respectively, and detecting and quantitating thus-formed complexes of capture probe and MR-proADM and/or MR-proANP, b. predicting renal endpoints by comparing the level of MR-proADM and/or MR-proANP the patient to a pre-determined statistically significant cutoff level of MR-proADM and/or MR-proANP in an ensemble of pre-determined samples in a population of primary chronic kidney disease patients whose primary chronic kidney disease reached renal endpoints, wherein said prediction is based on a statistically significant correlation of the level of MR-proADM and/or MR-proANP with the levels of the marker in the pre-determined samples.

10. A method for predicting the progression of primary chronic kidney disease in a patient comprising a. detecting and quantitating the level of one or more markers selected from the group consisting of MR-proADM of SEQ ID NO:4 and/or MR-proANP of SEQ ID NO:10 in a sample from said patient, wherein said detection and quantitation comprises contact the sample with a diagnostic assay reagent comprising a capture probe that specifically binds to MR-proADM and MR-proANP, respectively, and detecting and quantitating thus-formed complexes of capture probe and MR-proADM and/or MR-proANP, b. predicting the progression of primary chronic kidney disease or monitoring chronic kidney disease therapy by comparing the level of MR-proADM and/or MR-proANP in the patient to a predetermined statistically significant cutoff level of MR-proADM and/or MR-proANP in an ensemble of pre-determined samples in a population of primary chronic kidney disease patients whose primary chronic kidney disease progressed (progressor) or did not progress (non-progressor), wherein said prediction is based on a statistically significant correlation of the level of MR-proADM and/or MR-proANP with the levels of the marker in the pre-determined samples.

11. A method for classifying a patient suffering from primary chronic kidney disease into progressor or a non-progressor comprising a. detecting and quantitating the level of one or more markers selected from the group consisting of MR-proADM of SEQ ID NO:4 and/or MR-proANP of SEQ ID NO:10 in a sample from said patient, wherein said detection and quantitation comprises contact the sample with a diagnostic assay reagent comprising a capture probe that specifically binds to MR-proADM or MR-proANP, respectively, and detecting and quantitating thus-formed complexes of capture probe and MR-proADM and/or MR-proANP, b. classifying the patient as a progressor or non progressor by comparing the level of MR-proADM and/or MR-proANP in the patient to a predetermined statistically significant cutoff level of MR-proADM and/or MR-proANP in an ensemble of pre-determined samples in a population of primary chronic kidney disease patients whose primary chronic kidney disease progressed (progressor) or did not progress (non-progressor), wherein said classification is based on a statistically significant correlation of the level of MR-proADM and/or MR-proANP with the levels of the marker in the pre-determined samples with the level of MR-proADM and/or MR-proANP in a sample from said patient.

12. The method of claim 1 for monitoring kidney function.

13. The method of claim 5, wherein fragments of pro-Vasopressin selected from copeptin, vasopressin or neurophysin II are measured.

14. The method of claim 5, wherein fragments of Endothelin-1 selected from CT-proET-1, NT-proET-1, big-Endothelin-1 or Endothelin-1 are measured.

15. The method of claim 5, wherein the precursor of BNP or fragment thereof selected from proBNP or NT-proBNP are measured.

* * * * *

```
                        SEQUENCE LISTING

<160> NUMBER OF SEQ ID NOS: 10

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45
```

-continued

Ser Ser Ser Tyr Pro Thr Gly Leu Ala Asp Val Lys Ala Gly Pro Ala
        50              55                  60

Gln Thr Leu Ile Arg Pro Gln Asp Met Lys Gly Ala Ser Arg Ser Pro
65              70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
        130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 164
<212> TYPE: PRT
<213> ORGANISM: Homo sapiens

<400> SEQUENCE: 2

Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
                20                  25                  30

Thr Gly Leu Ala Asp Val Lys Ala Gly Pro Ala Gln Thr Leu Ile Arg
            35                  40                  45

Pro Gln Asp Met Lys Gly Ala Ser Arg Ser Pro Glu Asp Ser Ser Pro
        50                  55                  60

Asp Ala Ala Arg Ile Arg Val Lys Arg Tyr Arg Gln Ser Met Asn Asn
65                  70                  75                  80

Phe Gln Gly Leu Arg Ser Phe Gly Cys Arg Phe Gly Thr Cys Thr Val
                85                  90                  95

Gln Lys Leu Ala His Gln Ile Tyr Gln Phe Thr Asp Lys Asp Lys Asp
            100                 105                 110

Asn Val Ala Pro Arg Ser Lys Ile Ser Pro Gln Gly Tyr Gly Arg Arg
            115                 120                 125

Arg Arg Arg Ser Leu Pro Glu Ala Gly Pro Gly Arg Thr Leu Val Ser
        130                 135                 140

Ser Lys Pro Gln Ala His Gly Ala Pro Ala Pro Pro Ser Gly Ser Ala
145                 150                 155                 160

Pro His Phe Leu

<210> SEQ ID NO 3
<211> LENGTH: 20
<212> TYPE: PRT
<213> ORGANISM: Homo sapiens

<400> SEQUENCE: 3

Ala Arg Leu Asp Val Ala Ser Glu Phe Arg Lys Lys Trp Asn Lys Trp
1               5                   10                  15

Ala Leu Ser Arg

20

<210> SEQ ID NO 4
<211> LENGTH: 40
<212> TYPE: PRT
<213> ORGANISM: Homo sapiens

<400> SEQUENCE: 4

Glu Leu Arg Met Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser
            35                  40

<210> SEQ ID NO 5
<211> LENGTH: 52
<212> TYPE: PRT
<213> ORGANISM: Homo sapiens

<400> SEQUENCE: 5

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
            35                  40                  45

Pro Gln Gly Tyr
    50

<210> SEQ ID NO 6
<211> LENGTH: 153
<212> TYPE: PRT
<213> ORGANISM: Homo sapiens

<400> SEQUENCE: 6

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
            35                  40                  45

Glu Lys Met Pro Leu Glu Asp Glu Val Val Pro Pro Gln Val Leu Ser
        50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr Arg Arg
145                 150

<210> SEQ ID NO 7

<211> LENGTH: 126
<212> TYPE: PRT
<213> ORGANISM: Homo sapiens

<400> SEQUENCE: 7

```
Asn Pro Met Tyr Asn Ala Val Ser Asn Ala Asp Leu Met Asp Phe Lys
1               5                   10                  15
Asn Leu Leu Asp His Leu Glu Glu Lys Met Pro Leu Glu Asp Glu Val
            20                  25                  30
Val Pro Pro Gln Val Leu Ser Glu Pro Asn Glu Glu Ala Gly Ala Ala
        35                  40                  45
Leu Ser Pro Leu Pro Glu Val Pro Pro Trp Thr Gly Glu Val Ser Pro
50                  55                  60
Ala Gln Arg Asp Gly Gly Ala Leu Gly Arg Gly Pro Trp Asp Ser Ser
65                  70                  75                  80
Asp Arg Ser Ala Leu Leu Lys Ser Lys Leu Arg Ala Leu Leu Thr Ala
                85                  90                  95
Pro Arg Ser Leu Arg Arg Ser Ser Cys Phe Gly Gly Arg Met Asp Arg
            100                 105                 110
Ile Gly Ala Gln Ser Gly Leu Gly Cys Asn Ser Phe Arg Tyr
        115                 120                 125
```

<210> SEQ ID NO 8
<211> LENGTH: 28
<212> TYPE: PRT
<213> ORGANISM: Homo sapiens

<400> SEQUENCE: 8

```
Ser Leu Arg Arg Ser Ser Cys Phe Gly Gly Arg Met Asp Arg Ile Gly
1               5                   10                  15
Ala Gln Ser Gly Leu Gly Cys Asn Ser Phe Arg Tyr
            20                  25
```

<210> SEQ ID NO 9
<211> LENGTH: 98
<212> TYPE: PRT
<213> ORGANISM: Homo sapiens

<400> SEQUENCE: 9

```
Asn Pro Met Tyr Asn Ala Val Ser Asn Ala Asp Leu Met Asp Phe Lys
1               5                   10                  15
Asn Leu Leu Asp His Leu Glu Glu Lys Met Pro Leu Glu Asp Glu Val
            20                  25                  30
Val Pro Pro Gln Val Leu Ser Glu Pro Asn Glu Glu Ala Gly Ala Ala
        35                  40                  45
Leu Ser Pro Leu Pro Glu Val Pro Pro Trp Thr Gly Glu Val Ser Pro
50                  55                  60
Ala Gln Arg Asp Gly Gly Ala Leu Gly Arg Gly Pro Trp Asp Ser Ser
65                  70                  75                  80
Asp Arg Ser Ala Leu Leu Lys Ser Lys Leu Arg Ala Leu Leu Thr Ala
                85                  90                  95
Pro Arg
```

<210> SEQ ID NO 10
<211> LENGTH: 38
<212> TYPE: PRT
<213> ORGANISM: Homo sapiens

<400> SEQUENCE: 10

```
Pro Glu Val Pro Pro Trp Thr Gly Glu Val Ser Pro Ala Gln Arg Asp
1               5                   10                  15

Gly Gly Ala Leu Gly Arg Gly Pro Trp Asp Ser Ser Asp Arg Ser Ala
            20              25                  30

Leu Leu Lys Ser Lys Leu
            35
```